United States Patent
Bays et al.

(10) Patent No.: US 6,620,180 B1
(45) Date of Patent: Sep. 16, 2003

(54) POWERED LARYNGEAL CUTTING BLADE

(75) Inventors: F. Barry Bays, Jacksonville, FL (US); Gary Peters, Jacksonville, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 320 days.

(21) Appl. No.: 09/692,232

(22) Filed: Oct. 20, 2000

Related U.S. Application Data (63) Continuation of application No. 09/392,797, filed on Sep. 9, 1999, now abandoned.
(60) Provisional application No. 60/099,563, filed on Sep. 9, 1998.

(51) Int. Cl.[7] .............................................. A61B 17/32
(52) U.S. Cl. ...................................... 606/171; 606/180
(58) Field of Search .............................. 606/159, 160, 606/170, 171, 176, 167, 178, 179, 180; 604/22

(56) References Cited

U.S. PATENT DOCUMENTS

| | | |
|---|---|---|
| 4,203,444 A | 5/1980 | Bonnell et al. |
| 4,646,738 A | 3/1987 | Trott |
| 5,152,744 A | 10/1992 | Krause et al. |
| 5,217,479 A | 6/1993 | Shuler |
| 5,285,795 A | 2/1994 | Ryan et al. |
| 5,320,635 A | 6/1994 | Smith |
| 5,411,514 A | 5/1995 | Fucci et al. |
| 5,437,630 A * | 8/1995 | Daniel et al. ............... 604/22 |
| 5,514,151 A | 5/1996 | Fogarty et al. |
| 5,529,580 A | 6/1996 | Kusunoki et al. |
| 5,540,708 A | 7/1996 | Lim et al. |
| 5,593,416 A | 1/1997 | Donahue |
| 5,620,447 A | 4/1997 | Smith et al. |
| 5,690,660 A | 11/1997 | Kauker et al. |
| 5,709,698 A * | 1/1998 | Adams et al. ............... 604/22 |
| 5,741,287 A * | 4/1998 | Alden et al. ............... 604/22 |
| 5,833,702 A * | 11/1998 | Van Wyk et al. ......... 84/411 R |
| 5,851,212 A | 12/1998 | Zirps et al. |
| 5,916,231 A | 6/1999 | Bays |
| 5,922,003 A | 7/1999 | Anctil et al. |
| 6,183,433 B1 | 2/2001 | Bays |

FOREIGN PATENT DOCUMENTS

DE     3828478 A1     5/1989

\* cited by examiner

*Primary Examiner*—David O. Reip
*Assistant Examiner*—D. Jacob Davis

(57) ABSTRACT

A laryngeal cutting blade has an outer blade assembly including a tubular member having a bend closer to a proximal portion than a distal end, a hollow inner blade assembly rotatably received in the outer blade assembly for mounting to a powered handpiece and having a flexible portion disposed adjacent the bend and a suction passage extending through the inner blade assembly to permit aspiration of cut tissue, the angled configuration of the laryngeal cutting blade and toothed and smooth profile cutting ends therefore are particularly effective for debulking large, firm lesions and for delicate shaving of superficial lesions of the vocal cords after removal of bulk mass.

13 Claims, 13 Drawing Sheets

POWERED LARYNGEAL CUTTING BLADE

CROSS-REFERENCE TO RELATED PATENT APPLICATIONS

This application is a continuation application of prior U.S. patent application Ser. No. 09/392,797, filed Sep. 9, 1999 now abandoned, which claims priority to U.S. provisional application Ser. No. 60/099,563, filed Sep. 9, 1998, the entire disclosures of which are incorporated herein by reference.

BACKGROUND AND SUMMARY OF THE INVENTION

The present invention relates generally to instruments and methods for removing laryngeal lesions and, more particularly, to a surgical cutting instrument in the form of a powered shaver having a blade with an elongate inner member rotatably disposed within an elongate outer member having a cutting window at a distal end configured to permit laryngeal use including debulking of large, firm lesions and delicate shaving of superficial lesions directly on the vocal folds within the larynx.

Treatment for the removal of laryngeal lesions has progressed from cold steel techniques to the use of the $CO_2$ laser and KTP fiber directed laser. While the laser has become the standard treatment, there remain concerns such as airway fire and laser plume. Additionally, the use of lasers in removing laryngeal lesions can result in laser burn and post procedure edema.

Accordingly, it is an object of the present invention to provide an alternative treatment for the removal of laryngeal lesions that is safer, more accurate, and faster than laser tissue vaporization.

It is another object of the present invention to minimize post procedure edema by confining tissue injury to the superficial mucosa only.

Yet another object of the present invention is to reduce post operative pain and to speed recovery of the voice following removal of laryngeal lesions.

It is still another object of the present invention to address the fixed operating radius of the laryngoscope in laryngeal procedures by forming the distal tip of a powered shaver blade driven by a handpiece with an angle such that the radius of surgical access is increased to provide surgeons with the best view of the working tip plus enhanced access to lateral structures, the anterior commissure or the undersurface of the vocal folds.

Some of the advantages of the present invention over the prior art are that concerns such as laser burn, airway fire and laser plume are eliminated, post procedure edema is minimized, and post operative pain is reduced. In addition, equipment costs, set up and surgical time for the shaver are dramatically reduced versus the laser.

These and other objects and advantages can be accomplished individually or in combination by use of a powered shaver having a blade assembly in accordance with the present invention.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

DESCRIPTION OF THE PREFERRED EMBODIMENTS

Figures 1, 2:
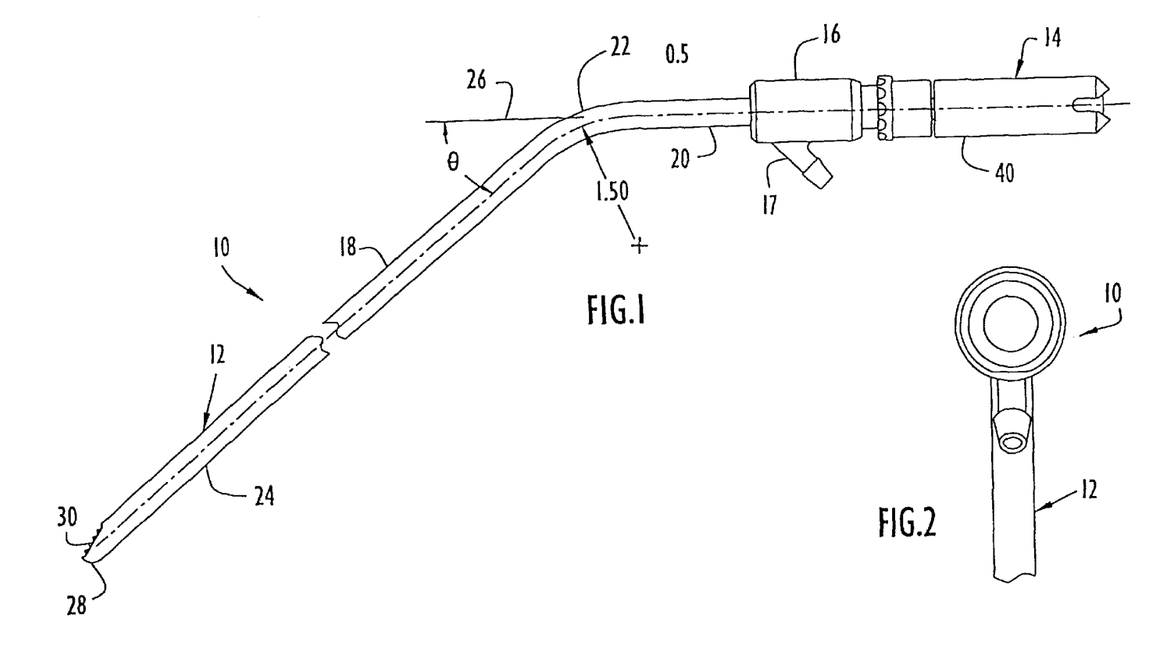
FIG. 1 is a side view, broken longitudinally, of a laryngeal blade according to the present invention.
FIG. 2 is a fragmentary rear view of the laryngeal blade shown in FIG. 1
Figure 3:
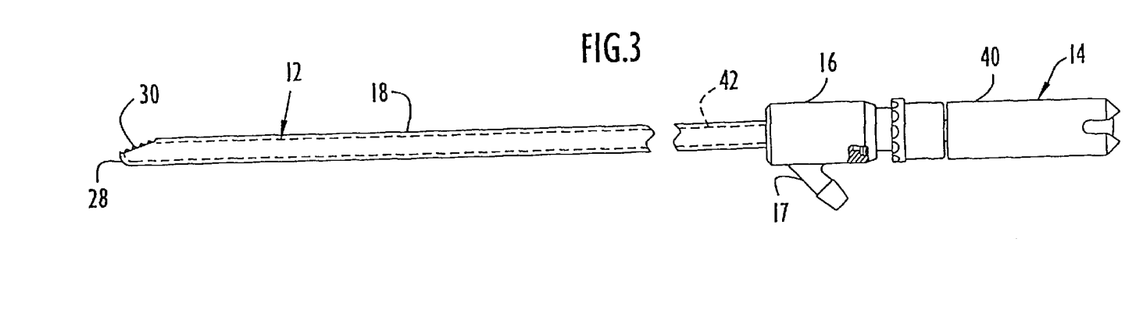
FIG. 3 is a side view, straightened and broken longitudinally, of the laryngeal blade shown in FIG. 1.
Figure 4:
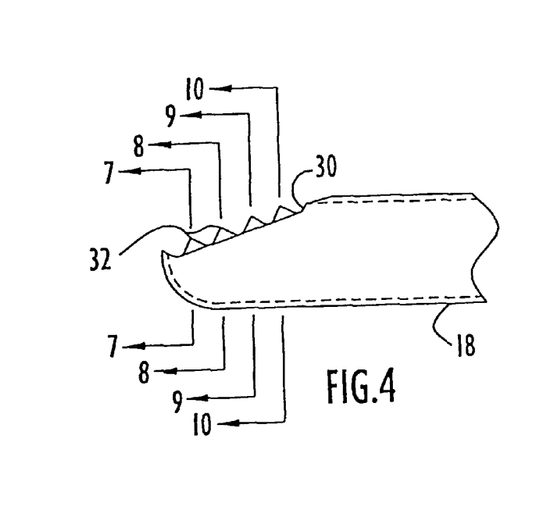
FIG. 4 is an enlarged fragmentary view of the distal end of the outer blade member.
Figure 5:
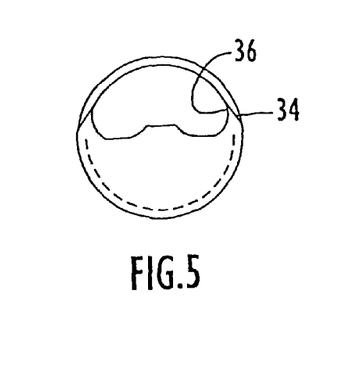
FIG. 5 is a front view of the outer blade member.
Figure 6:
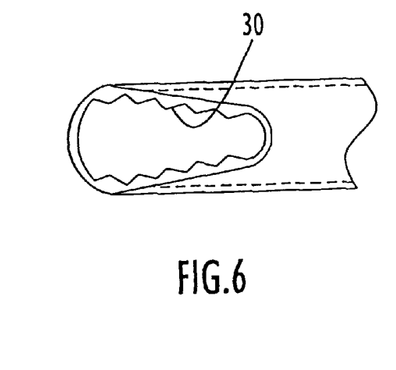
FIG. 6 is a fragmentary top view of the distal end of the outer blade member.
Figure 7:
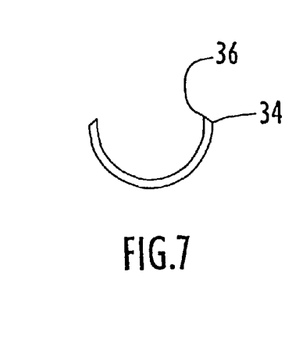
FIGS. 7–10 are sectional views taken through lines 7—7, 8—8, 9—9 and 10—10, respectively, in FIG. 4.
Figure 8:
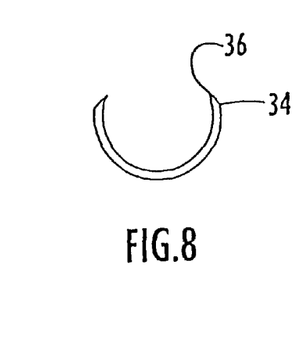
Figure 9:
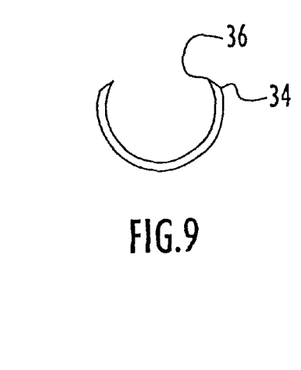
Figure 10:
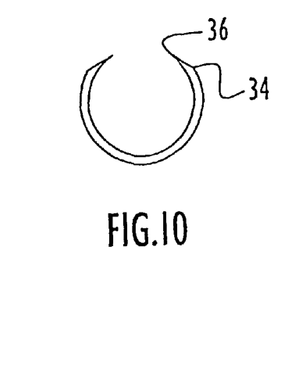
Figure 11:
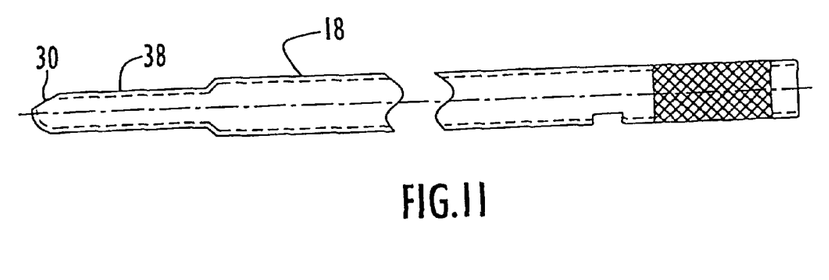
FIG. 11 is a side view, broken longitudinally, of a modification of an outer blade member according to the present invention.
Figure 12:
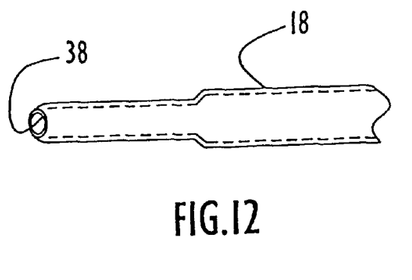
FIG. 12 is a fragmentary top view of the modified outer blade member shown in FIG. 11.
Figure 13:
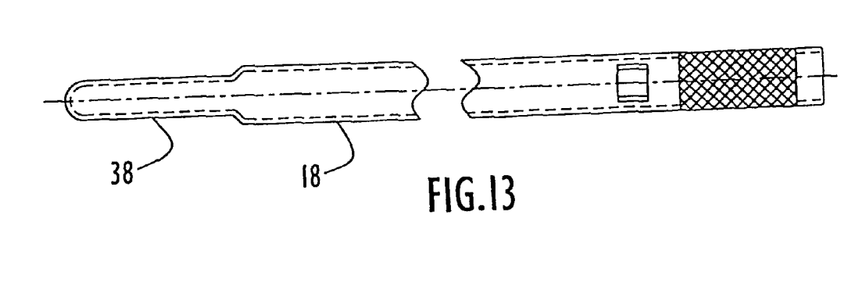
FIG. 13 is a bottom view of the modified outer blade member shown in FIG. 11.
Figure 14:
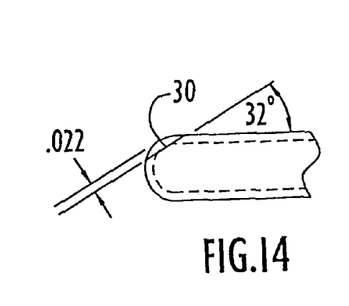
FIG. 14 is an enlarged fragmentary view of the distal end of the modified outer blade member shown in FIG. 11.
Figure 15:
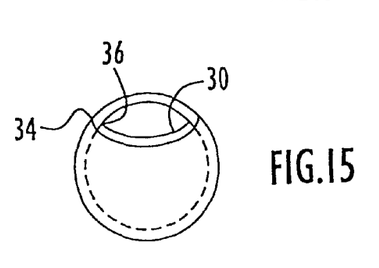
FIG. 15 is a front view of the modified outer blade member shown in FIG. 11.

A powered laryngeal cutting blade 10 according to the present invention is illustrated in FIGS. 1–3 and can be driven by any suitable handpiece such as the STRAIGHT-SHOT marketed by Xomed Surgical Products, Inc. and shown in U.S. Pat. No. 5,916,231 to Bays, the disclosure of which is incorporated herein by reference. The blade 10 includes an outer blade member or assembly 12 and a hollow inner blade member assembly 14 rotatably received within the outer blade member. Outer blade member 12 includes a hub 16 with an irrigation port or coupling 17 extending angularly therefrom and an outer tubular member or sleeve 18 having a proximal portion 20 of straight configuration extending distally from the hub to a proximal bend 22 connecting the proximal portion with a distal portion 24 oriented at an angle θ of about 45° relative to the longitudinal axis 26 of the proximal portion. The proximal bend 22 is closer to the proximal portion 20 than to the distal end 28 to provide desired spacing of the distal end from the proximal portion. Angled straight distal portion 24 of the outer tubular member extends downwardly from bend 22, looking at FIG. 1, a distance greater than the distance between bend 22 and the proximal portion and portion 24 extends to a rounded distal end 28 having an opening facing upwardly, away from the center of curvature of the bend, to define a cutting port or window 30. Dependent upon the anatomical situation and requirements, the window 30 can face in any desired direction (i.e. also downwardly or sidewards) and the outer blade member 12 can have multiple curves or bends, such as 22, along the length thereof.

As best seen in FIGS. 4–10, cutting port or window 30 is beveled and includes a plurality of teeth 32 along longitudinal sides thereof with an outer surface or edge 34 of the window being dull or blunt and an inner surface or edge 36 of the window being sharp. Four teeth 32 are shown on each side, however, any number of teeth can be used.

FIGS. 11–15 illustrate a modification of the outer assembly 12 to provide a smooth profile (as compared with the above described toothed laryngeal blade) wherein the outer. tubular member includes a necked distal portion 38 extending to a distal end having and a beveled circular cutting port or window 30 similar to that described above in that the inner surface or edge 36 is sharp but without any teeth. The necked distal portion, which is joined to the proximal portion, as an outer or external cross-sectional diameter smaller than the outer or external cross-sectional diameter of the proximal portion.

Figure 16:
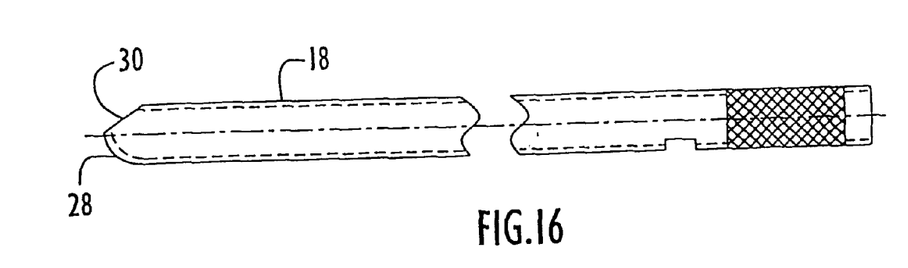
FIG. 16 is a side view, broken longitudinally, of another modification of an outer blade member according to the present invention.
Figure 17:
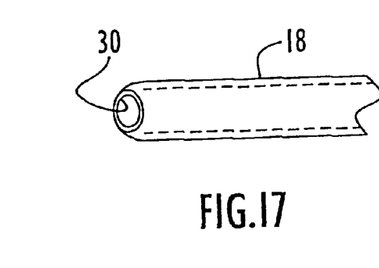
FIG. 17 is a fragmentary top view of the modified outer blade member shown in FIG. 16.
Figure 18:
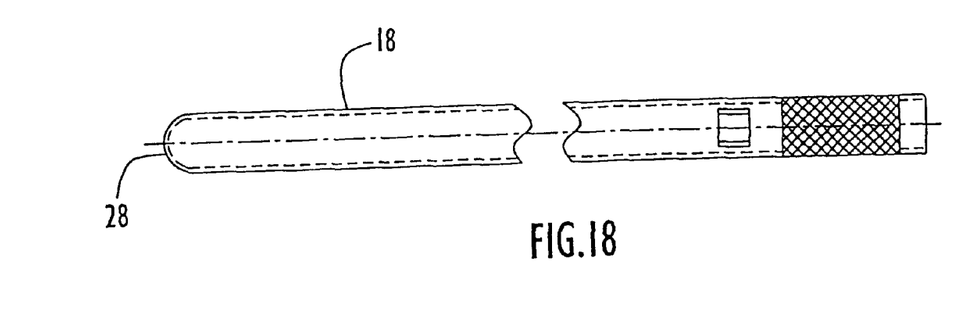
FIG. 18 is a bottom view, broken longitudinally, of the modified outer blade member shown in FIG. 16.
Figures 19, 20, 22:
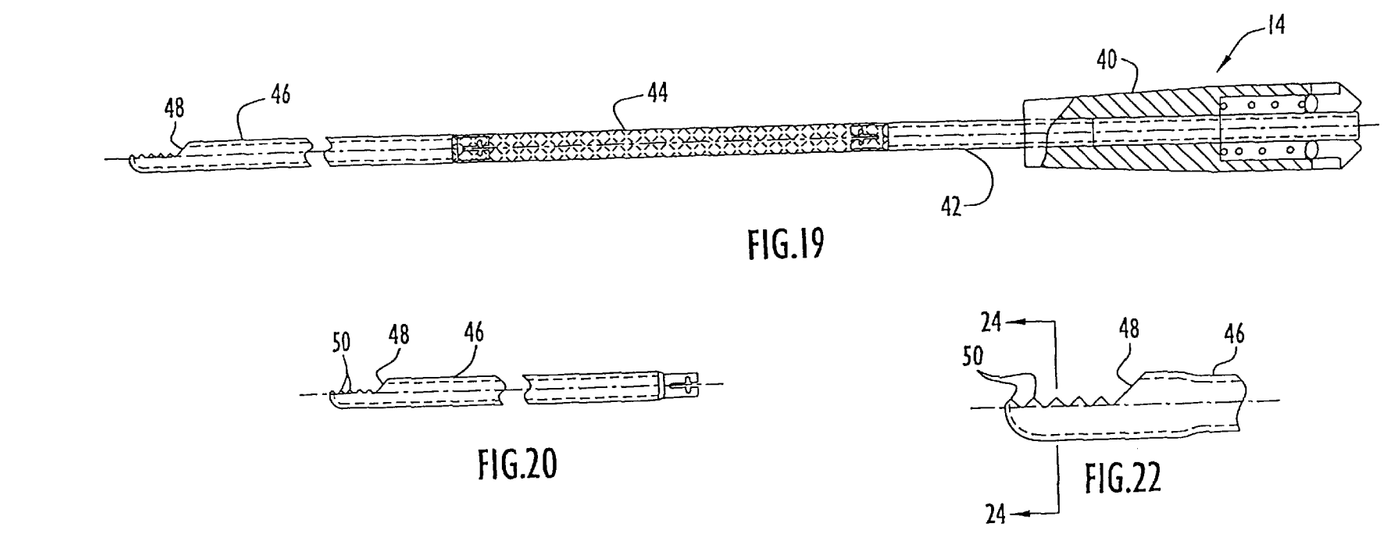
FIG. 19 is a side view, broken longitudinally, of an inner blade member or assembly for the laryngeal blade according to the present invention.
FIG. 20 is a side view, broken longitudinally, of a cutting tip at the distal end of the inner blade member.
FIG. 22 is an enlarged fragmentary side view of the cutting tip shown in FIG. 20.
Figure 21:
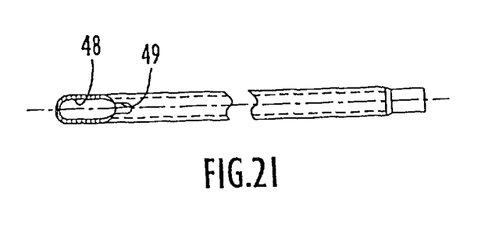
FIG. 21 is a top view of the cutting tip shown in FIG. 20.
Figure 23:
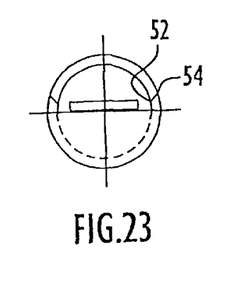
FIG. 23 is a front view of the cutting tip shown in FIG. 22.
Figure 24:
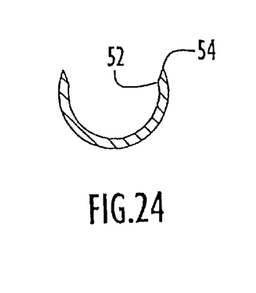
FIG. 24 is a sectional view taken through line 24—24 in FIG. 22.

FIGS. 16–18 illustrate another modification of the outer assembly 12 similar to that shown in FIGS. 11–15 but without a necked portion at a distal end.

FIGS. 19–24 illustrate an inner assembly 14 for the laryngeal blade according to the present invention, the inner assembly including a hub 40, a drive shaft 42 extending distally from the hub to a flexible coupling 44, and a cutting tip or cutter 46 extending distally from the flexible coupling. Cutting tip 46 includes a distal opening 48 defined by a peripheral edge with teeth 50 having a blunt inner surface or edge 52 and a sharp outer surface or edge 54. The distal opening communicates with a lumen defined by the inner assembly to permit tissue evacuation when the blade is connected with a source of suction. The inner assembly 14 has a size to rotate within the outer blade member 14 with sufficient annular space for irrigating fluid to pass between the inner and outer members from port 17 to the cutting tip via a flat 49 adjacent and aligned with opening 48 in order to prevent clogging of cut tissue in the lumen of the inner blade. The cut tissue is aspirated from the surgical site in a straight path through hub 40 to also prevent clogging and can be drawn through a STRAIGHTSHOT handpiece in a straight path.

Figure 25:
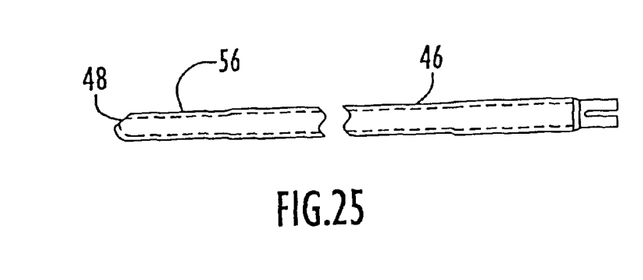
FIG. 25 is a side view, broken longitudinally, of a modification of a cutting tip or cutter for use with the laryngeal blade according to the present invention.
Figure 26:
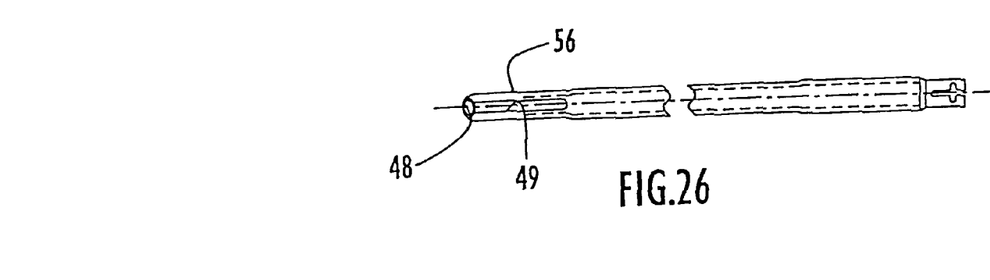
FIG. 26 is a top view of the modified cutter shown in FIG. 25.
Figure 27:
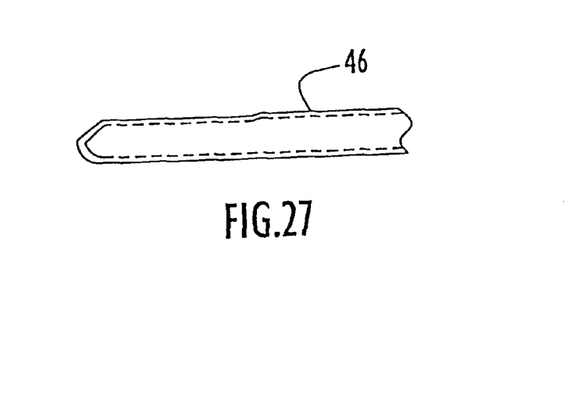
FIG. 27 is an enlarged fragmentary side view of the cutter shown in FIG. 25.
Figure 28:
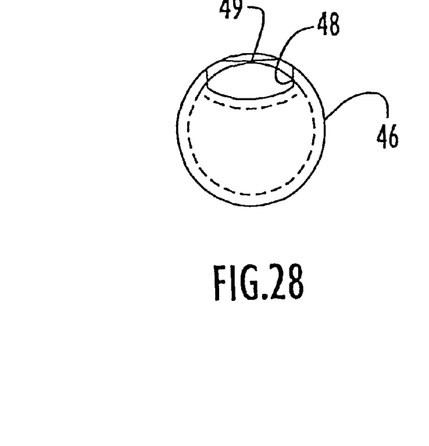
FIG. 28 is a front view of the cutter shown in FIG. 27.
Figure 29:
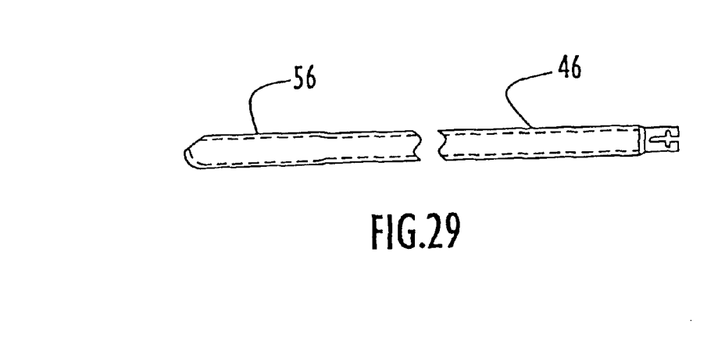
FIG. 29 is a side view, broken longitudinally, of yet another modification of a cutter for use with the laryngeal blade according to the present invention.
Figure 30:
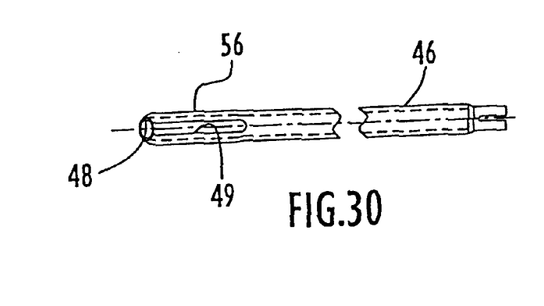
FIG. 30 is a top view of the modified cutter shown in FIG. 29.
Figure 31:
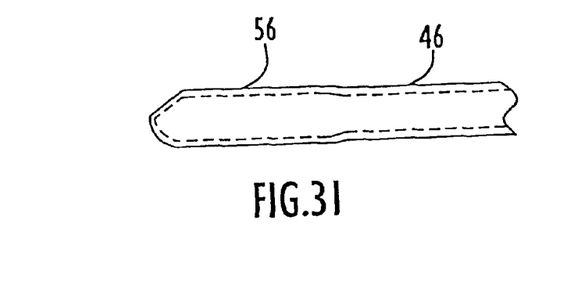
FIG. 31 is an enlarged fragmentary side view of the cutter shown in FIG. 29.
Figure 32:
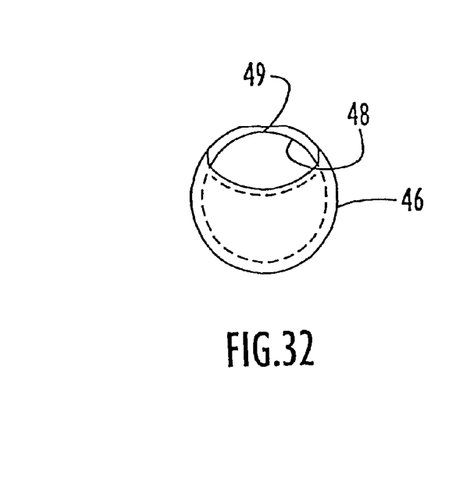
FIG. 32 is a front view of the cutter shown in FIG. 31.

FIGS. 25–28 illustrate a modification of a cutting tip 46 similar to that described above but with a necked distal portion 56 and a beveled circular distal opening or cutting tip 48 without any teeth. As shown in FIGS. 25 and 26, the necked distal portion 56 is joined to a proximal portion of the cutting tip and has an outer or external cross-sectional diameter smaller than the outer or external cross-sectional diameter of the proximal portion of the cutting tip. As also shown in FIGS. 25 and 26, the cutting tip 46 includes an intermediate portion joining the distal and proximal portions of the cutting tip, and the intermediate portion has an outer or external cross-sectional diameter smaller than the outer diameter of the proximal portion of the cutting tip and larger than the outer diameter of the distal portion of the cutting tip.

FIGS. 29–32 illustrate another modification of a cutting tip 46 similar to that shown in FIGS. 25–28 but with an enlarged distal portion 56 of larger diameter than the proximal portion of the cutting tip.

Figure 33:
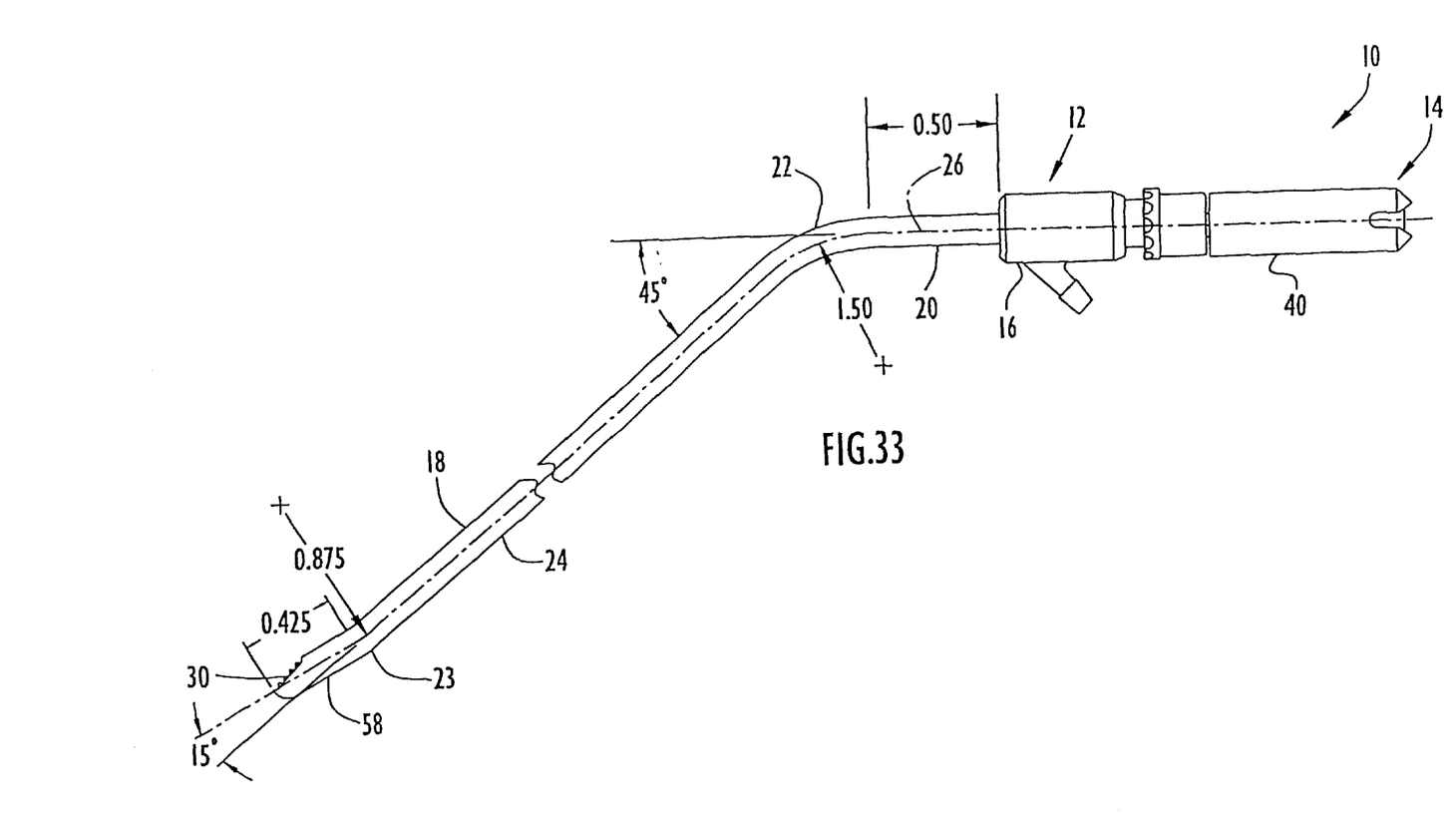
FIG. 33 is a modified laryngeal blade according to the present invention.
Figure 34:
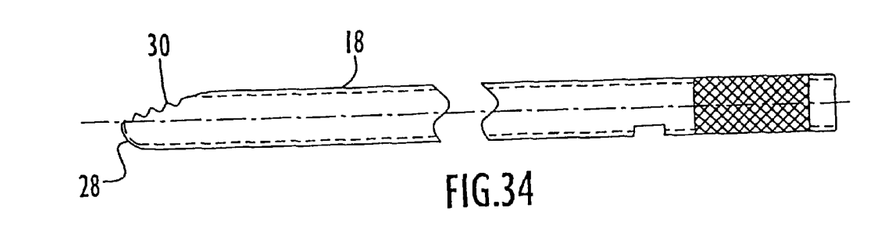
FIG. 34 is a side view, broken longitudinally, of the outer blade member shown in FIG. 33.
Figure 35:
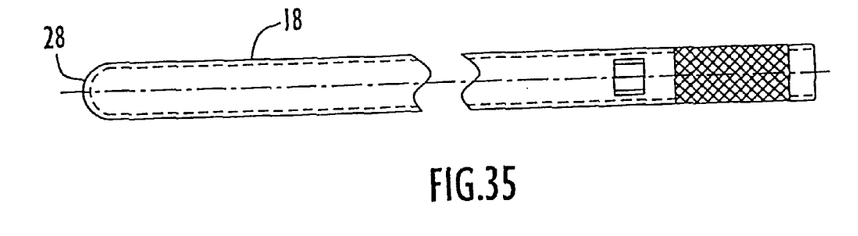
FIG. 35 is a bottom view, broken longitudinally, of the outer blade member shown in FIG. 34.
Figure 36:
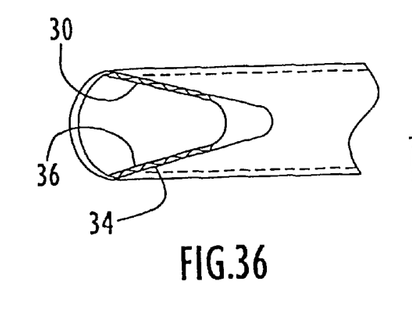
FIG. 36 is a fragmentary top view of the outer blade member shown in FIG. 34.

A modification of a laryngeal blade according to the present invention is shown in FIG. 33 at 10. The modified blade 10 is similar to that shown in FIG. 1 but with a distal bend 23 forming an angled distal portion 58 of relatively short length (e.g., about 0.425 inch) oriented at an angle of about 15° relative to distal portion 24 such that bend 23 is opposite the direction of bend 22 and the distal portion extends in the upward direction looking at FIG. 33 or any other desired direction as noted above dependent on anatomy. The angular orientation allows the surgeon the best view of the working tip plus enhanced access to lateral structures, the anterior commissure, the posterior commissure or the undersurface of the vocal folds.

Figure 37:
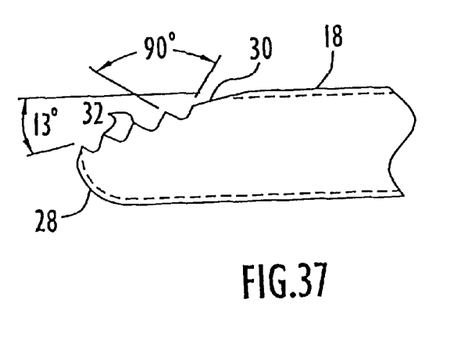
FIG. 37 is an enlarged fragmentary view of the distal end of the outer blade member shown in FIG. 34.
Figure 38:
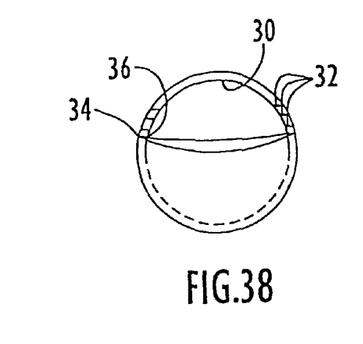
FIG. 38 is a front view of the outer blade member shown in FIG. 37.
Figure 39:
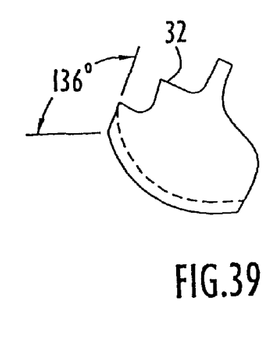
FIG. 39 is an enlarged fragmentary side view of the distal end of the outer blade member.
Figure 40:
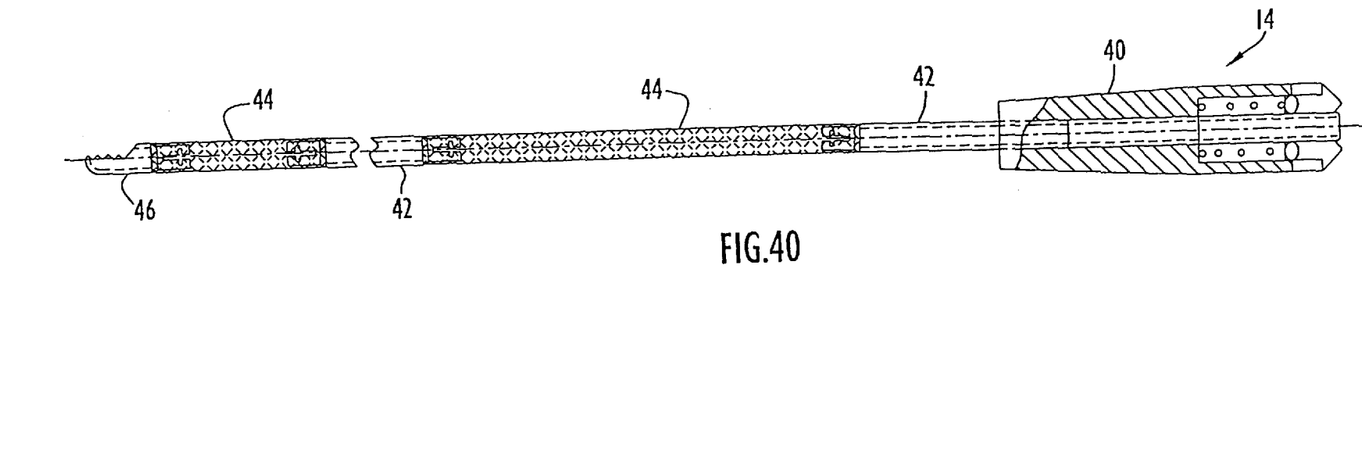
FIG. 40 is a side view, broken longitudinally, of an inner blade member for use with the laryngeal blade illustrated in FIG. 33.
Figure 41:
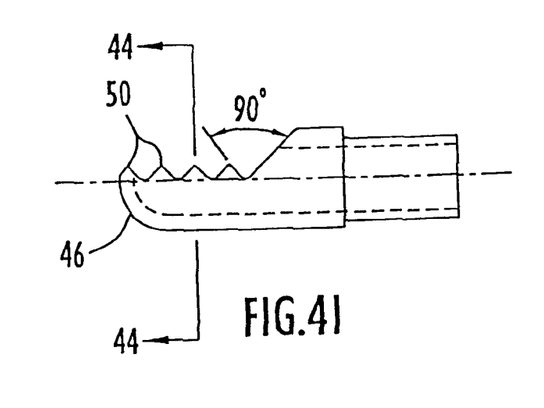
FIG. 41 is a side view of a cutting tip or cutter for use with the laryngeal blade according to the present invention.
Figure 42:
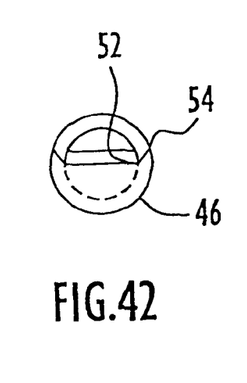
FIG. 42 is a front view of the cutter shown in FIG. 41.
Figure 43:
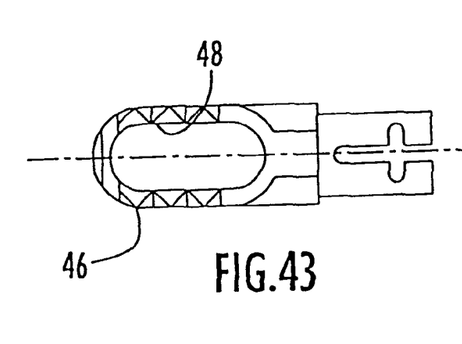
FIG. 43 is a top view of the cutter shown in FIG. 41.
Figure 44:
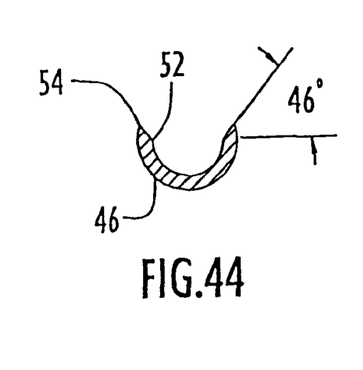
FIG. 44 is a sectional view taken through line 44—44 in FIG. 41.
Figure 45:
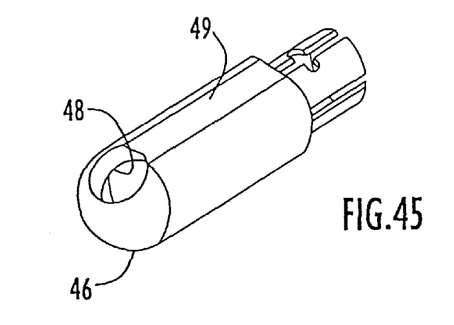
FIG. 45 is a perspective view of a modified cutter for use with the laryngeal blade according to the present invention.
Figure 46:
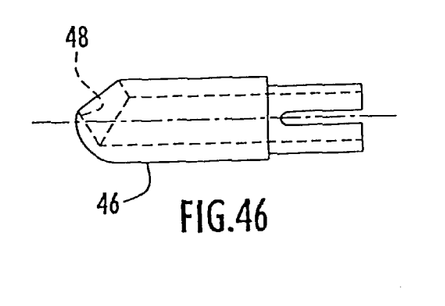
FIG. 46 is a side view of the modified cutter shown in FIG. 45.
Figure 47:
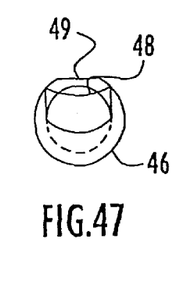
FIG. 47 is a front view of the cutter shown in FIG. 46.
Figure 48:
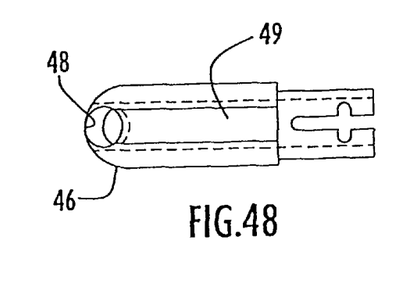
FIG. 48 is a top view of the cutter shown in FIG. 46.
Figure 49:
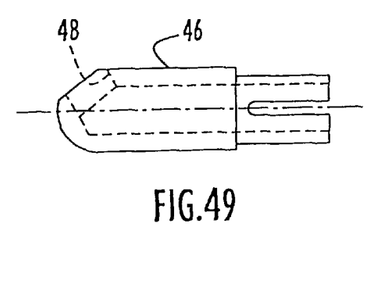
FIG. 49 is another view of the cutter shown in FIG. 46.

FIGS. 34–39 illustrate further details of the outer assembly 12 of laryngeal blade 10 shown in FIG. 33. Like the blade 10 shown in FIG. 1, window 30 of the blade shown in FIG. 33 is sharp along an inner surface or edge 36 and blunt or dull along an outer surface or edge 34. The window can be formed with teeth 32 as shown in FIGS. 34–39, or without teeth (e.g., in the ways described above for the blade shown in FIG. 1). FIG. 37 illustrates the cutting teeth extending upwardly at an angle of 13° from a distal end to a proximal end of the cutting window. FIG. 37 also illustrates the cutting teeth as having rearward surfaces angularly joined to forward surfaces thereof, with each of the rearward surfaces being angularly joined to a proximally adjacent forward surface at an angle of 90°. FIG. 39 illustrates the forward surfaces disposed at an angle of 136° to a central longitudinal axis of the outer tubular member Inner assembly 14 for the modified blade is similar to that described above but with a pair of flexible couplings 44 longitudinally spaced as shown in FIG. 40 to correspond to the bends in outer tubular member 44 of the modified blade. FIGS. 41–49 illustrate exemplary cutting tips 46 which can be used with the inner assembly 14. FIG. 41 illustrates the cutting teeth as having proximal surfaces angularly joined to distal surfaces thereof, with each of the proximal surfaces being angularly joined to a proximally adjacent distal surface at an angle of 90°. FIG. 44 illustrates the blunt inner edge 52 joined to the sharp outer edge 54 by a surface disposed at an angle of 46°.

In use, general anaesthesia is typically induced and the airway secured by endotracheal tube (ETT) intubation or tracheotomy, if indicated. Size of the endotracheal tube will vary depending on airway conditions (presence of stenosis) and intubation technique. In adults, a small, cuffed 5.0 mm or 5.5 mm ETT is adequate for ventilation and allows access for surgical instrumentation. With stenotic lesions, smaller cuffless ETTs may be required. In this situation, the laryngoscope may accommodate powered instrumentation, a rigid telescope, and the ETT, allowing for uninterrupted surgery.

The laryngoscope is positioned to allow access to the anatomy to be excised with the powered shaver 10. Access to the anterior commissure and subglottic region may be accomplished using an anterior commissure laryngoscope. Visualization can be enhanced using 0° or 30° rigid telescopes and conventional video imaging systems. Console settings for the powered handpiece should preferably be set on "oscillate" mode with a maximum speed set at about 1000 rpms for superficial lesions or those located near or on the vocal folds. Use of "variable" mode of foot switch operation is preferred as it allows for more controlled excision with slow, single revolutions when needed. The laryngeal blade is then securely attached to the powered handpiece. Irrigation (e.g., a 1000 cc or 3000 cc bag at 6 foot elevation) is preferably used with the blade and allowed to flow continuously throughout the procedure to prevent clogging. Wall suction levels may be adjusted to provide enough vacuum to allow the blade to remove tissue at an efficient rate (e.g., 150 mm to 180 mm Hg). Use of an in-line tissue trap is desirable to capture specimens for pathology.

Figure 50:
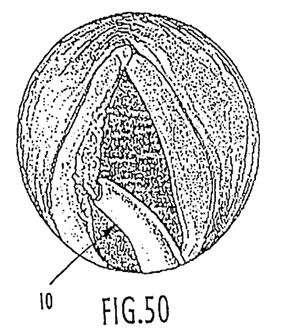
FIGS. 50 and 51 illustrate use of the laryngeal blade according to the present invention for removal of papilloma from the vocal fold.
Figure 51:
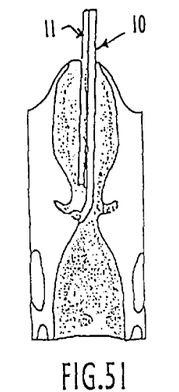
Figure 52:
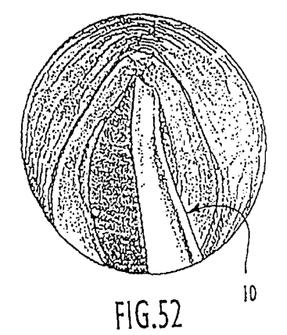
FIG. 52 illustrates use of the laryngeal blade according to the present invention for removal of papilloma from the anterior commissure.

The laryngeal shaver blade 10 can be utilized for a number of procedures. In FIGS. 50 and 51, the laryngeal blade 10 is shown in use, along with a laryngoscope or endoscope 11, for delicate removal of papilloma from the vocal fold. Oscillation speeds of between about 60 and about 1000 rpm are believed to offer the most precise result and, for the most precise excisions, tissue can be pulled into the opening and with light pressure on the variable foot switch amputated with single blade revolutions. With the window configuration of the present invention, discrete lesions can be accurately removed with trauma limited to the superficial mucosa. For greatest precision when removing papilloma from the anterior commissure, endoscopic visualization with a 30° endoscope is recommended as shown in FIG. 52.

Figure 53:
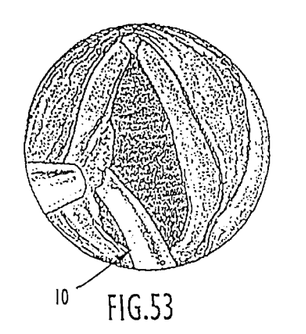
FIGS. 53 and 54 illustrate use of the laryngeal blade according to the present invention for removal of lesions located on the undersurface of the vocal fold.
Figure 54:
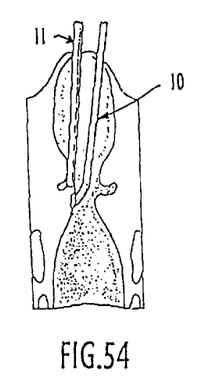

The angled-tip design of the laryngeal blade 10 shown in FIG. 33 allows excellent access for removal of lesions located on the under surface of the vocal fold as shown in FIGS. 53 and 54. With an oblique endoscope and/or aid of suction to elevate the vocal fold, delicate excision of pathology can be achieved.

Figure 55:
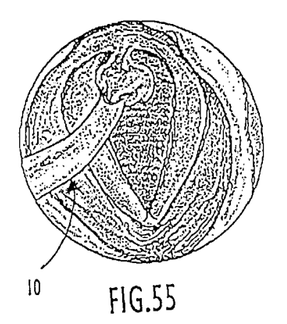
FIGS. 55 and 56 illustrate use of the laryngeal blade according to the present invention for removal of vocal fold polyps.
Figure 56:
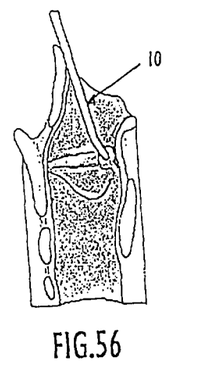
Figure 57:
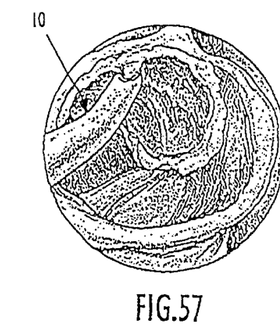
FIG. 57 illustrates use of the laryngeal blade according to the present invention for delicate sculpting of edges after removal of an airway tumor using an aggressive toothed blade.

Vocal fold polyps can be quickly and precisely removed without tearing or trauma to peripheral tissues as shown in FIGS. 55 and 56. After debulking airway tumors using the aggressive toothed laryngeal blades shown in FIGS. 1–10, 19–24 and 33–44, edges can be more delicately sculpted with the smooth laryngeal blades shown in FIGS. 11–18, 25–32 and 45–49.

The toothed laryngeal blades according to the present invention are particularly effective for debulking of large, firm lesions, such as exophytic or fibrous lesions, airway tumors, granulation tissue, tracheal lesions and metastatic tumors. The smooth laryngeal blades according to the present invention are particularly effective for delicate shaving of superficial lesions off the vocal folds, such as papilloma, without tearing or trauma and after removal of bulk mass by the toothed laryngeal blades, for sculpting edges.

The tubular portions of the blade can be formed of any suitable materials and can have any suitable dimensions. For example, the tubular portions can be made of stainless steel with the outer tube being about 0.156 in diameter and about 11.0 inches long, the inner tube or drive shaft being rotatable within the outer tube with sufficient space for irrigating fluid to pass therebetween.

Inasmuch as the present invention is subject to many variations, modifications, and changes in detail, it is intended that all subject matter discussed above or shown in the accompanying drawings be interpreted as illustrative only and not be taken in a limiting sense.

What is claimed is:

1. A laryngeal cutting blade comprising:
an outer blade assembly including an outer tubular member having a proximal portion for mounting to a powered handpiece and a distal portion extending distally to a rounded distal end having a cutting window therein, said cutting window being configured with a plurality of cutting teeth extending along longitudinal sides of said cutting window, said cutting teeth having a blunt outer edge and a sharp inner edge, said distal portion of said outer tubular member being cylindrical, said proximal portion of said outer tubular member being cylindrical, and said distal portion of said outer tubular member having an external diameter smaller than an external diameter of said proximal portion of said outer tubular member;

a hollow inner blade assembly rotatably received in said outer blade assembly and having a drive shaft for mounting to the powered handpiece and a cutting tip coupled to said drive shaft, said cutting tip including a cutting opening disposed adjacent said cutting window of said outer blade assembly, said cutting opening being configured with a plurality of cutting teeth extending along longitudinal sides of said cutting opening, said cutting teeth of said cutting opening having a blunt inner edge and a sharp outer edge; and a suction passage extending through said inner blade assembly to permit aspiration of cut tissue through said cutting blade.

2. A laryngeal cutting blade as recited in claim 1 wherein said cutting tip includes a proximal portion coupled to said drive shaft and a distal portion having said cutting opening therein joined to said proximal portion of said cutting tip, said proximal portion of said cutting tip is cylindrical, said distal portion of said cutting tip is cylindrical, and said distal portion of said cutting tip has an external diameter smaller than an external diameter of said proximal portion of said cutting tip.

3. A laryngeal cutting blade as recited in claim 2 wherein said cutting tip includes an intermediate portion joining said distal portion of said cutting tip to said proximal portion of said cutting tip, said intermediate portion having an external diameter smaller than said external diameter of said proximal portion of said cutting tip and larger than said external diameter of said distal portion of said cutting tip.

4. A laryngeal cutting blade as recited in claim 2 wherein said cutting opening is beveled and said cutting opening and said cutting window are circular.

5. A laryngeal cutting blade comprising
an outer blade assembly including an outer tubular member having a proximal portion for mounting to a powered handpiece and a distal portion extending distally to a rounded distal end having a beveled cutting window therein, said cutting window being circular and having a blunt outer edge and a sharp inner edge, said beveled cutting window being disposed at an angle of 32° to a central longitudinal axis of said outer tubular member;

a hollow inner blade assembly rotatably received in said outer blade assembly and having a drive shaft for mounting to the powered handpiece and a cutting tip coupled to said drive shaft, said cutting tip including a beveled cutting opening disposed adjacent said cutting window of said outer blade assembly, said cutting opening being circular and having a blunt inner edge and a sharp outer edge; and a suction passage extending through said inner blade assembly to permit aspiration of cut tissue through said cutting blade.

6. A laryngeal cutting blade comprising:
an outer blade assembly including an outer tubular member having a proximal portion for mounting to a powered handpiece and a distal portion extending distally to a rounded distal end having a beveled cutting window therein, said cutting window having a blunt outer edge and a sharp inner edge, said cutting window being configured with a plurality of cutting teeth extending along longitudinal sides of said cutting window, said cutting teeth of said cutting window extending upwardly at an angle of 13° from a distal end to a proximal end of said cutting window;

a hollow inner blade assembly rotatably received in said outer blade assembly and having a drive shaft for mounting to the powered handpiece and a cutting tip coupled to said drive shaft, said cutting tip including a cutting opening disposed adjacent said cutting window of said outer blade assembly and having a blunt inner edge and a sharp outer edge, said cutting opening being configured with a plurality of cutting teeth extending along longitudinal sides of said cutting opening; and a suction passage extending through said inner blade assembly to permit aspiration of cut tissue through said cutting blade.

7. A laryngeal cutting blade as recited in claim 6 wherein said cutting teeth of said cutting opening extend upwardly at an angle from a distal end to a proximal end of said cutting opening.

8. A laryngeal cutting blade as recited in claim 6 wherein each of said cutting teeth of said cutting window has a forward surface and a rearward surface angularly joined to said forward surface, each of said rearward surfaces being angularly joined to a proximally adjacent one of said forward surfaces at an angle of 90°, said forward surfaces being disposed at an angle of 136° to a central longitudinal axis of said outer tubular member.

9. A laryngeal cutting blade as recited in claim 6 wherein each of said cutting teeth of said cutting opening has a distal surface and a proximal surface angularly joined to said distal surface, each of said proximal surfaces being angularly joined to a proximally adjacent one of said distal surfaces at an angle of 90°, said blunt inner edge of said cutting opening being joined to said sharp outer edge of said cutting opening by a surface disposed at an angle of 46°.

10. A laryngeal cutting blade comprising:
an outer blade assembly including an outer tubular member having a proximal portion for mounting to a powered handpiece and a distal portion extending distally to a rounded distal end having a cutting window therein, said cutting window being configured with a plurality of cutting teeth extending along longitudinal sides of said cutting window, said cutting teeth having a blunt outer edge and a sharp inner edge, each of said cutting teeth of said cutting window having a forward surface and a rearward surface angularly joined to said forward surface, each of said rearward surfaces being angularly joined to a proximally adjacent one of said forward surfaces at an angle of 90°, said forward surfaces being disposed at an angle of 136° to a central longitudinal axis of said outer tubular member;

a hollow inner blade assembly rotatably received in outer blade assembly and having a drive shaft for mounting to the powered handpiece and a cutting tip coupled to said, drive shaft, said cutting tip including a cutting opening disposed adjacent said cutting window of said outer blade assembly, said cutting opening being configured with a plurality of cutting teeth extending along longitudinal sides of said cutting opening, said cutting teeth of said cutting opening having a blunt inner edge and a sharp outer edge; and a suction passage extending through said inner blade assembly to permit aspiration of cut tissue through said cutting blade.

11. A laryngeal cutting blade as recited in claim 10 wherein each of said cutting teeth of said cutting opening has a distal surface and a proximal surface angularly joined to said distal surface, each of said proximal surfaces being angularly joined to a proximally adjacent one of said distal surfaces at an angle of 90°, said blunt inner edge of said cutting teeth of said cutting opening being joined to said sharp outer edge of said cutting teeth of said cutting opening by a surface disposed at an angle of 46°.

12. A laryngeal cutting blade as recited in claim 11 wherein said cutting teeth of said cutting window extend upwardly at an angle of 13° from a distal end to a proximal end of said cutting window and said cutting teeth of said cutting opening extend upwardly at an angle from a distal end to a proximal end of said cutting opening.

13. A laryngeal cutting blade comprising:
   an outer blade assembly including an outer tubular member having a proximal portion for mounting to a powered handpiece and a distal portion extending distally to a rounded distal end having a cutting window therein, said cutting window being configured with a plurality of cutting teeth extending along longitudinal sis of said cutting window, said cutting teeth having a blunt outer edge and a sharp inner edge, said cutting teeth of said cutting window extending upwardly at an angle from a distal end to a proximal end of said cutting window to be disposed non-parallel to a central longitudinal axis of said outer tubular member;

a hollow inner blade assembly rotatably received in said outer blade assembly and having a drive shaft for mounting to the powered handpiece and a cutting tip coupled to said drive shaft, said cutting tip including a cutting opening disposed adjacent said cutting window of said outer blade assembly, said cutting opening being configured with a plurality of cutting teeth extending along longitudinal sides of said cutting opening, said cutting teeth of said cutting opening having a blunt inner edge and a sharp outer edge, said cutting teeth of said cutting opening extending upwardly at an angle from a distal end to a proximal end of said cutting opening to be disposed non-parallel to a central longitudinal axis of said drive shaft; and a suction passage extending through said inner blade assembly to permit aspiration of cut tissue through said cutting blade.

* * * * *